United States Patent
Musha

[11] Patent Number: 6,067,464
[45] Date of Patent: May 23, 2000

[54] ELECTRODE

[75] Inventor: Toshimitsu Musha, Machida, Japan

[73] Assignee: Brain Functions Laboratory, Inc., Japan

[21] Appl. No.: 08/943,743

[22] Filed: Oct. 3, 1997

[30] Foreign Application Priority Data

Oct. 7, 1996 [JP] Japan ................................. 8-265720
Jun. 25, 1997 [JP] Japan ................................. 9-168691

[51] Int. Cl.$^7$ .................................................. A61B 5/0478
[52] U.S. Cl. .......................... 600/383; 600/386; 600/397; 600/544
[58] Field of Search .................................. 600/382, 383, 600/386, 393, 395, 397, 544; 607/153

[56] References Cited

U.S. PATENT DOCUMENTS

| | | | |
|---|---|---|---|
| 3,831,598 | 8/1974 | Tice | 607/153 |
| 3,998,213 | 12/1976 | Price | 600/383 |
| 4,102,331 | 7/1978 | Grayzel et al. | 600/397 |
| 4,109,648 | 8/1978 | Larke et al. | 600/383 |
| 4,126,126 | 11/1978 | Bare et al. | 600/397 |
| 4,237,886 | 12/1980 | Sakurada et al. | |
| 4,473,492 | 9/1984 | Schmolka | 607/153 |
| 4,735,207 | 4/1988 | Nambu et al. | |
| 5,143,071 | 9/1992 | Keusch et al. | 600/397 |
| 5,143,089 | 9/1992 | Alt et al. | |
| 5,218,973 | 6/1993 | Weaver et al. | |
| 5,326,341 | 7/1994 | Lew et al. | |
| 5,348,006 | 9/1994 | Tucker | 600/397 |
| 5,357,957 | 10/1994 | Itil et al. | 600/386 |
| 5,411,527 | 5/1995 | Alt et al. | |
| 5,474,065 | 12/1995 | Meathrel et al. | |
| 5,727,549 | 3/1998 | Suda et al. | 600/393 |
| 5,755,230 | 5/1998 | Schmidt et al. | 600/544 |

FOREIGN PATENT DOCUMENTS 2274396  7/1994  United Kingdom ................... 600/397

OTHER PUBLICATIONS

Kiyoaki Katahika, Electrical Properties of Carbon Fiber and its Biomedical Application, Fukushima Medical Journal, vol. 39 , pp. 467–473 (1989).

T. Shigemitsu, T. Nagata, G. Matsumoto and S. Tsukahara, Electrical Properties Of The Carbon Fibre Electrode And Its Application, Medical & Biological Engineering & Computing, vol. 18, pp. 359–362 (1980).

Yu Satoh, Studies On ERG Electrodes With Reference To The Oscillatory Potential, Japanese Journal of Clinical Ophthalmology, vol. 25, pp. 525–542 9 (1971).

Daizo Yonemura and Isao Hasui, About the History of ERG and the Recorder, Ophthalmology, vol. 13, No. 4, pp. 455–461.

*Primary Examiner*—Lee Cohen
*Attorney, Agent, or Firm*—Rader, Fishman & Grauer

[57] ABSTRACT

An electrode and a method for measuring bio-electric waves are provided in which the electrode comprises a support member, a piece of absorbent fiber projecting from the support member and a non-corrosive lead coupled to the piece of absorbent fiber. Improved electrical contact between the electrode and the subject's skin is provided by allowing the piece of absorbent fiber to absorb an electrically conductive fluid.

22 Claims, 5 Drawing Sheets

ELECTRODE

BACKGROUND OF THE INVENTION

This invention relates to electrodes. The present invention is primarily intended for use with live subjects and has application in, for example, the recordation of bio-electric waves such as electroencephalographic ("EEG") brain waves.

Heretofore, most electrodes used for measuring brain waves have required the application of some kind of paste or gel to establish electrical contact between the electrode and the scalp. After measurement, the paste or gel remains on the patient's scalp and in his hair and must be washed off. The process of applying and washing the paste or gel is an added burden for patients, especially those who may be suffering from dementia, for example. In addition, the paste or gel which adhere to the patient's scalp and hair can increase his stress level, thereby interfering with brain wave measurements.

In view of the foregoing, it would be desirable to provide an electrode which does not require the use of paste or gel to establish electrical contact.

It would also be desirable to provide an electrode which is easy to use.

SUMMARY OF THE INVENTION

It is an object of the present invention to provide an electrode which does not require the use of paste or gel to establish electrical contact.

It is also an object of the present invention to provide an electrode which is easy to use.

These and other objects are accomplished by electrode comprising a support member, a piece of absorbent fiber projecting from the support member and a non-corrosive lead coupled to the piece of absorbent fiber.

BRIEF DESCRIPTION OF THE INVENTION

The above and other objects and advantages of the invention will be apparent upon consideration of the following detailed description, taken in conjunction with the accompanying drawings, in which reference characters refer to like parts throughout and in which.

DETAILED DESCRIPTION

Figure 1:
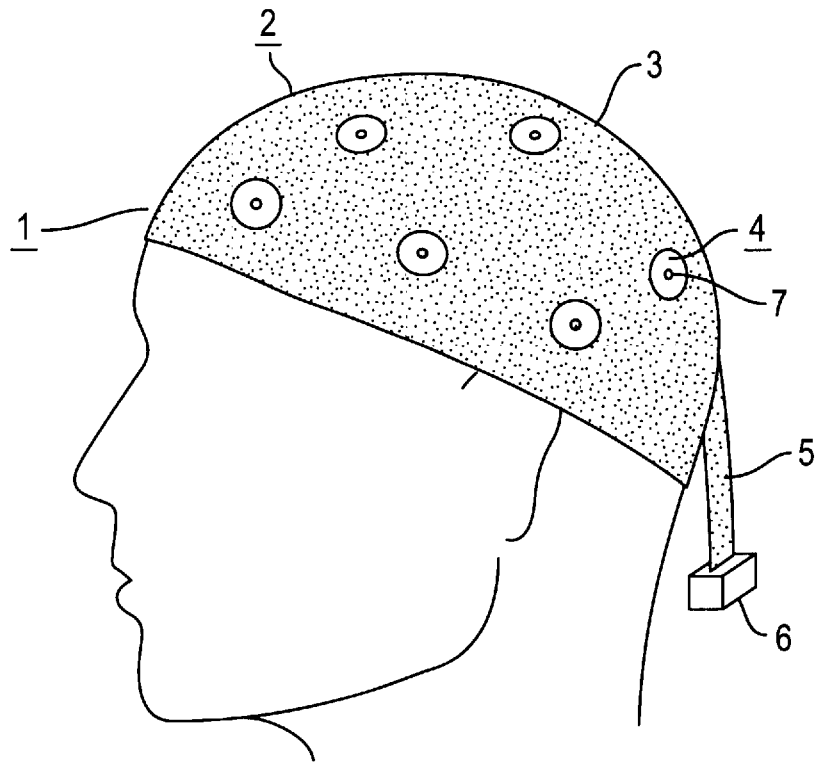
FIG. 1 is an exterior view of the head of a patient wearing a headpiece which incorporates an implementation of the electrode of the present invention.

FIG. 1 shows an exterior view of head 1 of a patient wearing headpiece 2 which includes net cap 3 and incorporates a plurality of electrodes 4. Net cap 3 can be made of an elastic material and can, therefore, fit various sized heads. Electrode 4 is shown with insertion hole 7, which allows electrically conductive fluid to be introduced into electrode 4, both before and during use, without removing electrode 4 from contact with the patient's skin. Also shown are leads 5 coupled between each electrode 4 and connector 6. Connector 6 is used to correct leads 5 to external processing equipment (not shown in FIG. 1).

Figure 2:
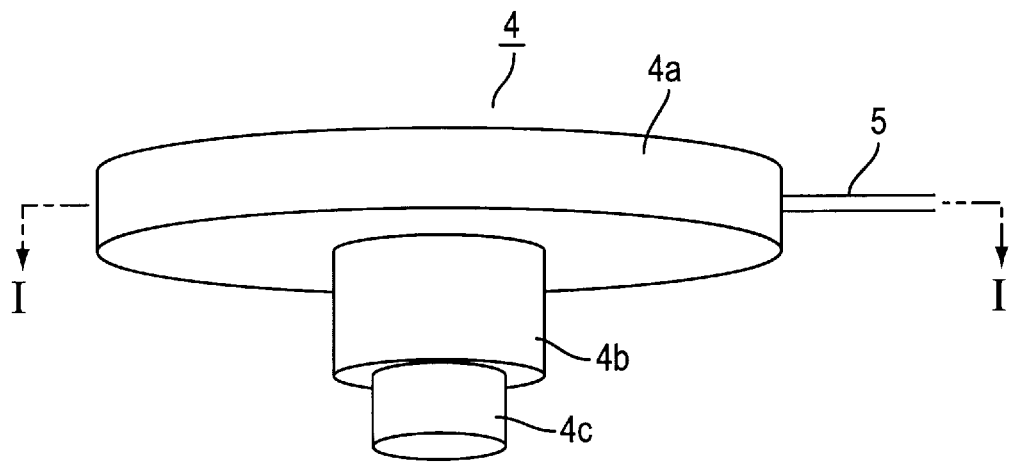
FIG. 2 is a angle view of an implementation of the electrode of the present invention.

FIG. 2 is a angle view of an implementation of electrode 4 comprising disk-shaped support member 4a with concentric cylindrical projection 4b and a non-through hole. Piece of absorbent fiber 4c is mounted in the non-through hole.

Figure 8A:
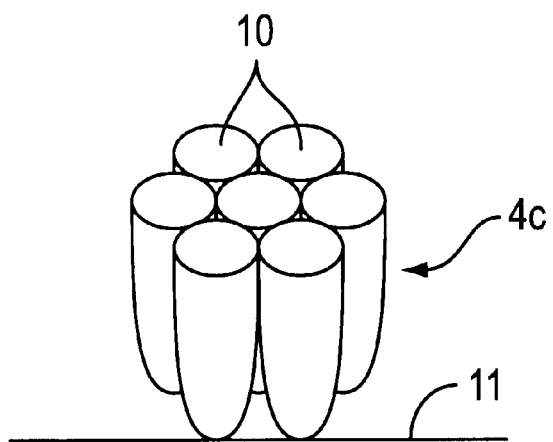
FIGS. 8A and 8B show angle views of another implementation of the piece of absorbent fiber and the electrode of the present invention.
Figure 8B:
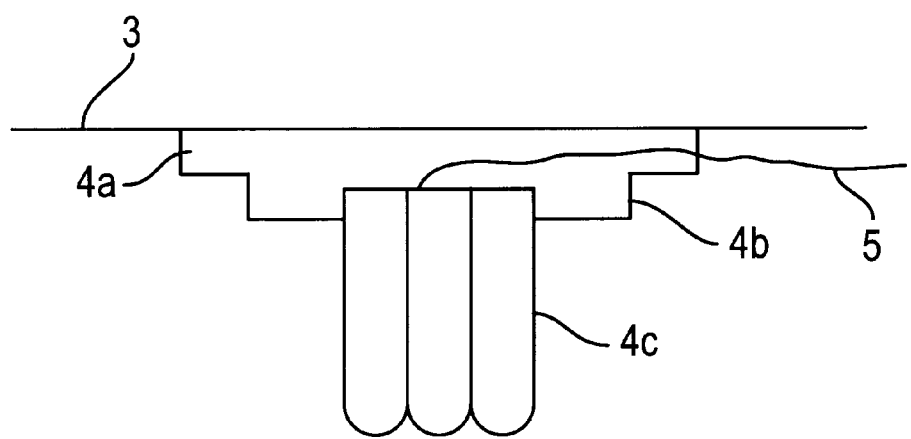

FIG. 8A is an angle view of another implementation of piece of absorbent fiber 4c which comprises bundle of hard felt rods 10 (preferably of diameter of about 2 mm and with rounded tips for making contact with a patient's skin 11). Hard felt rods 10 may be impregnated with carbon powder for increased conductivity. FIG. 8B shows electrode 4 coupled to net cap 3. Electrode 4 comprises support member 4a, projection 4b and piece of absorbent fiber 4c. Also shown are leads 5 which may be coupled to piece of absorbent fiber 4c.

Support member 4a and projection 4b are fabricated of insulating materials (such as ceramics) and/or preferably materials which are also light-weight, such as plastics. Also, synthetic fibers and felt which have had their surfaces heat treated may be used.

Piece of absorbent fiber 4c may be, for example, felt. One reason why felt is preferred as piece of absorbent fiber 4c is that, along with its high absorption, it prevents evaporation and drying out of the electrically conductive fluid during measurement. In addition to felt, cotton and synthetic fibers may be used.

The electrically conductive fluid may also comprise various skin conditioners, such as menthol, counterirritant materials such as Frescolat, anti-inflammatory agents such as Candilla wax and astringents such as zinc sulfate.

Saline solution is preferably used as the electrically conductive fluid because, in addition to greatly increasing the electrical conductivity, saline solution is basically the same as sweat and therefore the need for the patient to wash his hair after removal of the electrodes is eliminated.

Figure 3:
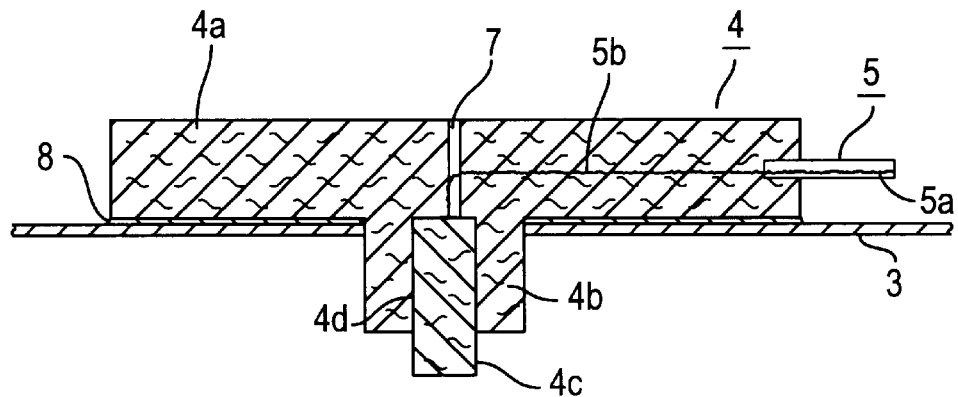
FIG. 3 is a cross-section view of an implementation of the electrode of the present invention.

FIG. 3 is a cross-section view along line I—I of an implementation of electrode 4 shown in FIG. 2. Projection 4b is shown with non-through hole 4d. Insertion hole 7 goes through support member 4a and reaches non-through hole 4d. Electrode 4 may be fastened to net cap 3 by adhesive 8.

Leads 5 may, for example, comprise insulator 5a surrounding bundle 5b of conductors, such as carbon fibers, which make electrical contact with the bottom of non-through hole 4d through support member 4a.

Figure 4:
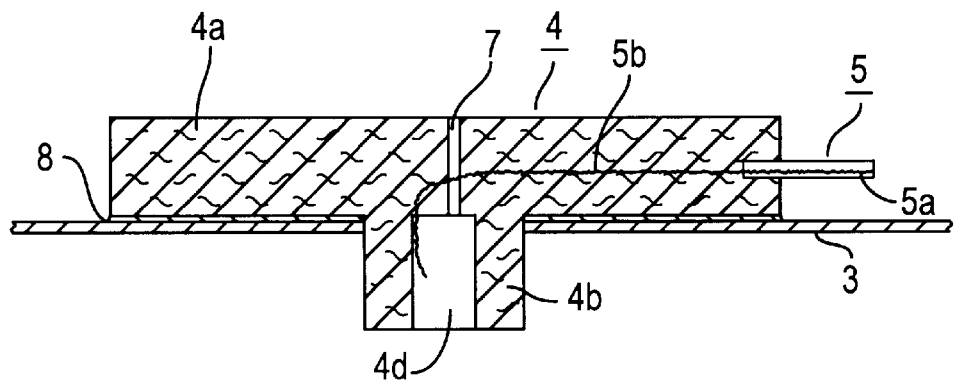
FIG. 4 is a cross-section view of another implementation of the electrode of the present invention.

FIG. 4 is a cross-section view of another implementation of electrode 4 of the present invention.

In FIG. 4, electrode 4 is shown without absorbent fiber 4c. Bundle 5b of conductors project from a wall of non-through hole 4d.

Figure 5:
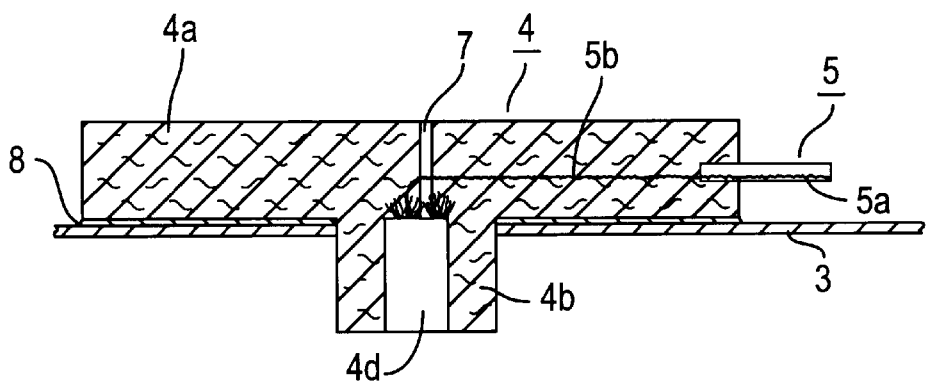
FIG. 5 is a cross-section view of yet another implementation of the electrode of the present invention.

FIG. 5 is a cross-section view of yet another implementation of electrode 4. Here, bundle 5b of conductors is molded to and projects from the surface of non-through hole 4d.

In use, after piece of absorbent fiber 4c is inserted into non-through hole 4d in projection 4b, electrically conductive fluid is allowed to be absorbed by piece of absorbent fiber 4c. As can be seen from FIG. 3, for example, the depth of non-through hole 4d is less than the length of piece of absorbent fiber 4c, which projects from non-through hole 4d. Thus, projection 4b does not come in direct contact with the patient's skin and does not cause any unpleasant sensation. Piece of absorbent fiber 4c swells as it absorbs the electrically conductive fluid and therefore does not easily fall out of non-through hole 4d, even when electrode 4 is suspended upside down. An increased density of piece of absorbent fiber 4c also contributes to making it difficult for piece of absorbent fiber 4c to fall out of non-through hole 4d.

Because bundle 5b of conductors projects from a wall of non-through hole 4d, a signal strong enough for further processing can be obtained from the patient's brain waves when electrode 4 is brought into contact with the patient's scalp as the signal travels the low resistance path through the electrically conductive fluid absorbed in piece of absorbent fiber 4c. Bundle 5b of conductors in leads 5 is preferably fabricated from carbon fibers, which are strong and resistant to corrosion by electrically conductive fluids such as saline solution.

As shown in FIG. 5, bundle 5b of conductors is molded to and projects from the surface of non-through hole 4d, which provides better electrical conduction between piece of absorbent fiber 4c and bundle 5b of conductors.

Figure 6:
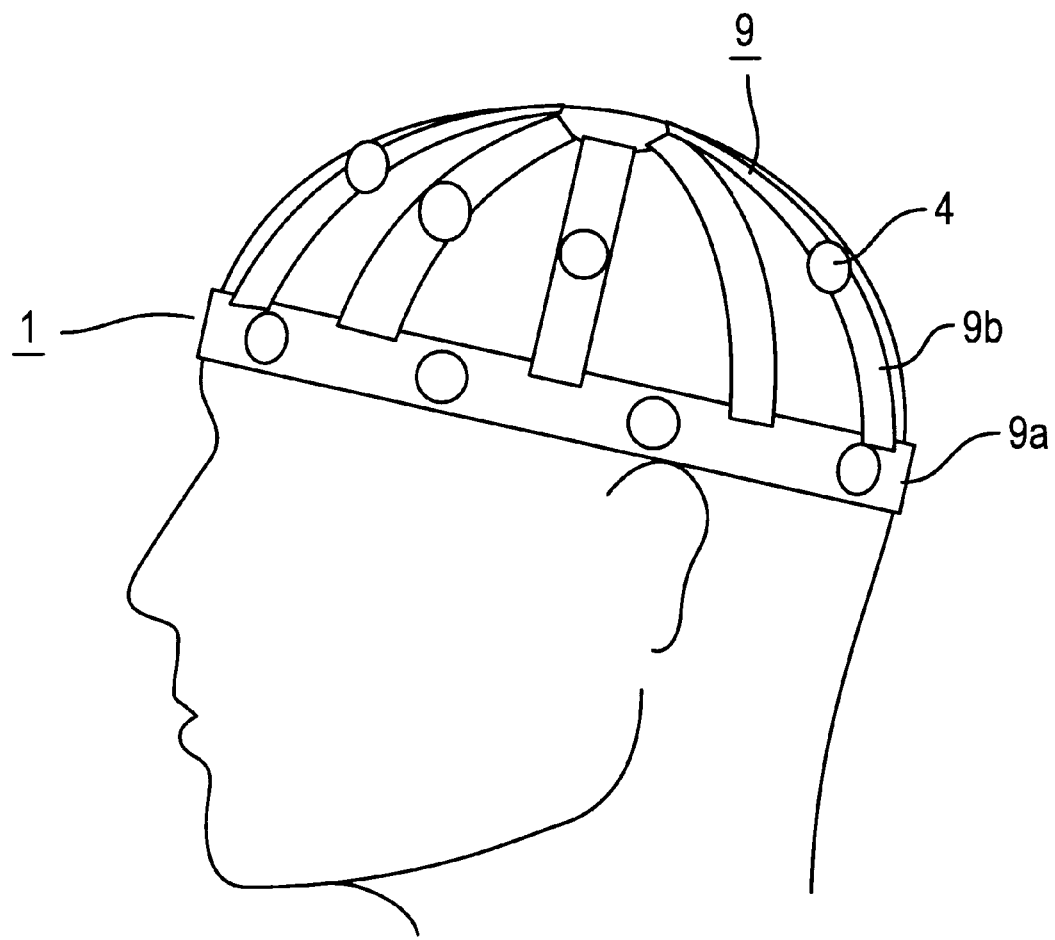
FIG. 6 is an exterior view of the head of a patient wearing a modified headpiece which incorporates an imolementation of the electrode of the present invention.

FIG. 6 is an exterior view of the head of a patient wearing modified headpiece 9 which incorporates an implementation of electrode 4. Headpiece 9 is comprised of headband 9a and umbrella frame bands 9b to which electrodes 4 are coupled.

Figure 7A:
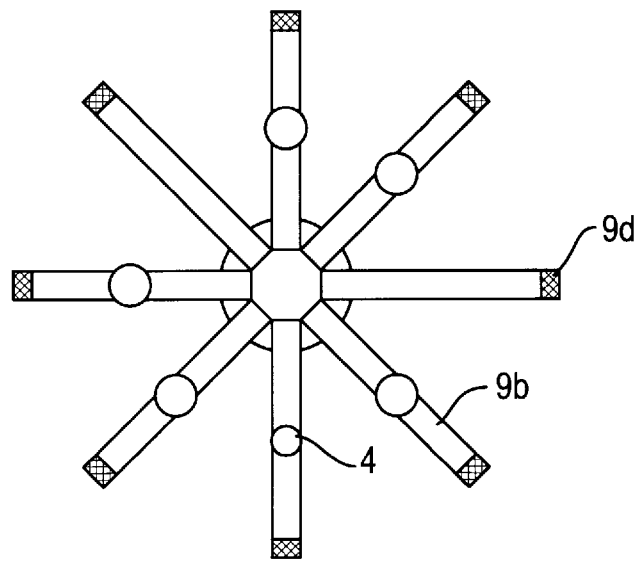
FIGS. 7A and 7B show the component parts of the headpiece of FIG. 6.
Figure 7B:
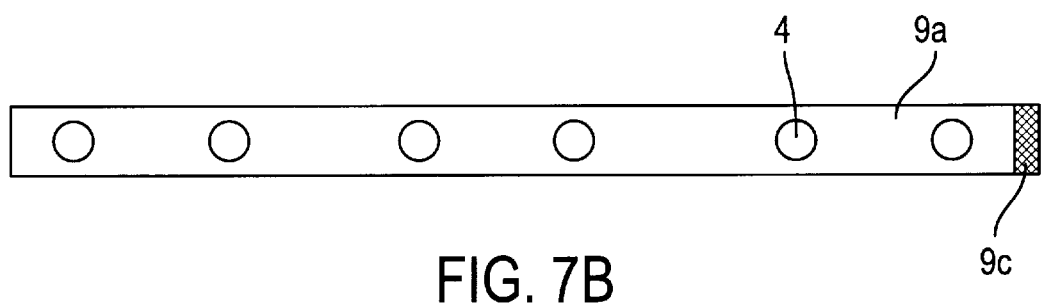

FIGS. 7A and 7B show the component parts (i.e., headband 9a and umbrella frame bands 9b) of headpiece 9 of FIG. 6. Also shown are fasteners 9c and 9d, such as Velcro tape, at the ends of headband 9a and umbrella frame bands 9b. Using fasteners 9c and 9d, it is possible to assemble headband 9a and umbrella frame bands 9b into headpiece 9 of FIG. 6.

To provide greater freedom of movement, the electrodes may be coupled to a wireless transmitter. The wireless transmitter may, for example, be located on the headpiece or net cap. Thus, the electric signals produced on the electrodes may be transmitted to external processing equipment through the wireless transmitter.

What is claimed is:

1. An electrode comprising:
   a support member;
   a projection, concentrically projecting from the support member, the projection having a non-through hole;
   a piece of absorbent fiber projecting from said non-through hole of said projection; and
   a non-corrosive lead coupled to said piece of absorbent fiber,
   wherein said absorbent fiber has absorbed an electrically conducting fluid.

2. The electrode of claim 1 wherein said non-corrosive lead comprises a carbon fiber.

3. The electrode of claim 1 wherein said electrically conductive fluid further includes a saline solution.

4. The electrode of claim 1 wherein said support member comprises hardened felt.

5. The electrode of claim 1 wherein said non-corrosive lead is molded into said support member.

6. The elect rode of claim 1 wherein said support member includes an insertion hole through which fluid may be added to said piece of absorbent fiber.

7. The electrode of claim 1 coupled to a headpiece.

8. The electrode of claim 7, wherein said headpiece comprises a wireless transmitter for transmitting the electrical signal produced on said non-corrosive lead.

9. The electrode of claim 1 wherein said piece of absorbent fiber comprises a bundle of hard felt rods.

10. The electrode of claim 9 wherein said bundle of hard felt rods is impregnated with carbon powder.

11. The electrode according to claim 1, wherein the piece of absorbent fiber is removably inserted into the non-through hole.

12. An electrode comprising:
    a support member;
    a projection, concentrically projecting from the support member, the projection having a non-through hole;
    a piece of absorbent fiber projecting from said non-through hole on the projection, wherein said piece of absorbent fiber is felt, wherein said piece of absorbent fiber has absorbed an electrically conductive fluid; and
    a non-corrosive lead coupled to said piece of absorbent fiber.

13. The electrode of claim 12 wherein said non-corrosive lead comprises a carbon fiber.

14. The electrode of claim 12 wherein said electrically conductive fluid further includes a saline solution.

15. The electrode of claim 12 wherein said non-corrosive lead is molded into said support member.

16. The electrode of claim 12 wherein said support member includes an insertion hole through which fluid may be added to said piece of absorbent fiber.

17. The electrode of claim 12 coupled to a headpiece.

18. The electrode of claim 17, wherein said headpiece comprises a wireless transmitter for transmitting the electrical signal produced on said non-corrosive lead.

19. The electrode according to claim 12, wherein the piece of absorbent fiber is removably inserted into the non-through hole.

20. A method for measuring bio-electric waves, said method comprising the steps of:
    contacting the skin of a subject with an electrode, wherein said electrode comprises a support member, a projection concentrically projecting from the support member, the projection having a non-through hole, and a piece of absorbent fiber projecting from said non-through hole of said projection and a non-corrosive lead coupled to said piece of absorbent fiber, wherein said piece of absorbent fiber has absorbed an electrically conductive fluid; and
    measuring the electric signal produced on said non-corrosive lead.

21. The method of claim 20 further comprising the step of:
    transmitting the electric signal produced on said non-corrosive lead via a wireless transmitter.

22. The method according to claim 20, wherein the piece of absorbent fiber is removably inserted into the non-through hole.

* * * * *